United States Patent [19]

Zawadzki

[11] Patent Number: 4,915,938

[45] Date of Patent: Apr. 10, 1990

[54] HAIR TREATING COMPOSITION

[76] Inventor: Mary E. Zawadzki, Nine Chauncy St., Apt. 54, Cambridge, Mass. 02138

[21] Appl. No.: 120,336

[22] Filed: Nov. 13, 1987

[51] Int. Cl.$^4$ .............................................. A61K 7/06
[52] U.S. Cl. .................................... 424/70; 424/71; 424/DIG. 1; 424/DIG. 2
[58] Field of Search ............... 424/47, 70, 71, DIG. 1, 424/DIG. 2; 132/7

[56] References Cited

U.S. PATENT DOCUMENTS

| | | |
|---|---|---|
| 4,240,450 | 12/1980 | Grollier et al. . |
| 4,311,626 | 1/1982 | Ona et al. . |
| 4,342,742 | 8/1982 | Sebag et al. ............................ 424/70 |
| 4,409,267 | 10/1983 | Ichinohe et al. . |
| 4,419,391 | 12/1983 | Tanaka et al. . |
| 4,425,364 | 1/1984 | Vanlerberghe et al. ............. 424/358 |
| 4,490,356 | 12/1984 | Sebag et al. . |
| 4,559,385 | 12/1985 | Huhn et al. . |
| 4,586,518 | 5/1986 | Cornwall et al. . |
| 4,601,902 | 7/1986 | Fridd et al. . |
| 4,618,689 | 10/1986 | Traver et al. . |
| 4,631,207 | 12/1986 | Price . |
| 4,658,049 | 4/1987 | Nakano et al. . |

FOREIGN PATENT DOCUMENTS

| | | |
|---|---|---|
| 0095238 | 4/1983 | European Pat. Off. . |
| 58605 | 4/1982 | Japan . |
| 144179 | 8/1983 | Japan . |

Primary Examiner—Ellis P. Robinson
Assistant Examiner—P. J. Ryan

[57] ABSTRACT

Hair-treating composition comprising an aqueous dispersion of a mixture of an amino- and hydroxy- or alkoxy-functional silicone with an amino-functional silicone and a cross-linking agent comprising a water-soluble compound containing at least two carboxyl groups.

5 Claims, No Drawings

HAIR TREATING COMPOSITION

This invention relates to a composition comprising a novel liquid aqueous dispersion containing a combination of two types of siloxane polymers together with a water soluble compound containing at least two carboxyl groups dissolved in the aqueous phase of said dispersion. The composition is useful either alone or in combination with additional components as a cosmetic composition for treating hair, for example as a hair set.

There have previously been proposed in U.S. Pat. Nos. 4,409,267, 4,419,391, and 4,631,207, a variety of amino functional polysiloxanes for treating fabrics or fibers or for waterproofing masonry. In Huhn et al. U.S. Pat. No. 4,559,385, there were described complex mixtures of hydroxy functional polysiloxanes, amino-functional polysiloxanes, organo silanes, and a condensation catalyst for treating a variety of natural and synthetic fibers. Hair treating compositions containing amino functional polysiloxanes have been described in Cornwall et al. U.S. Pat. Nos. 4,586,518, Fridd et al. 4,601,902, and Traver et al. 4,618,689. In Sebag et al. U.S. Pat. Nos. 4,342,742 and Sebag et al. 4,490,356, there were described polysiloxane products having any one of a variety of hydrophilic groups including amino functional and carboxy-functional groups bonded to the silicon atoms by a decamethylene chain. The products were said to be useful in a variety of hair treating compositions including shampoos, dyes, setting lotions and waving compositions.

In Japanese Patent 58605 (1982) there was described a composition containing an amino functional polysiloxane along with a dibasic carboxylic acid or an amino acid for use in cosmetics applied to hair and skin. In Japanese Patent 144179 (1983) there was described a process for treating cloth to make it durably water repellent by applying to it in sequence an amino functional polyalkoxysilane, followed by carboxy-or carboxy ester-functional polysiloxane. Ona et al. U.S. Pat. No. 4,311,626 described a composition for treating natural or synthetic fibers and fabrics to impart a combination of properties durable to washing and dry cleaning; the composition contained an amino functional polysiloxane free from alkoxy and hydroxy groups, and a carboxy functional polysiloxane. Nakano et al. U.S. Pat. No. 4,658,049 described a carboxy-functional polysiloxane having a variety of uses, and published European Patent Application No. 0095238 described the application to hair of a composition comprising (1) a polysiloxane containing a functional group that provides attachment to the hair, (2) a surfactant (3) a freeze thaw stabilizer and (4) water. Grollier et al. U.S. Pat. No. 4,240,450 described compositions for treating hair or skin comprising a combination of a cationic polymer with an anionic polymer, the polymers being conventional carbon type polymers free from silicon or siloxane groups.

It has now been found that a composition comprising a liquid aqueous dispersion of two different types of polysiloxanes together with a cross-linking agent dissolved in the aqueous phase in the form of a water-soluble compound containing at least two carboxyl groups possesses unique advantages for treating hair, as in a cosmetic composition. The composition is characterized by solidifying or "drying" rapidly within a few minutes after application to hair at a temperature of 20-30° C. and by being readily removable from hair by shampooing or washing with soap. In addition, the composition, when applied to hair, serves to retain the curl and set of the hair for an extended period even when exposed to conditions of high humidity and subjected to repeated combing. Other agents conventionally present in hair treating compositions may optionally be added to provide, for example, a hair conditioner. The dispersion, with or without optional additives, when applied to hair, provides not only set retention but also high sheen, desirable tactile properties, and ease of combing.

The composition of the present invention includes as one of the two types of polysiloxanes an amino functional polysiloxane which includes one or more hydroxy or alkoxy groups bonded directed to silicon (Type I) and having the following composition:

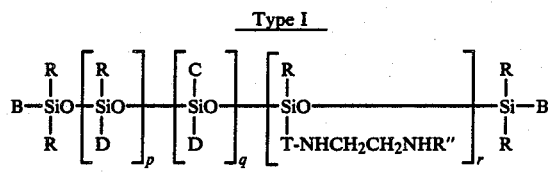

Type I in which
is a monovalent hydrocarbon group having 1 to 20 carbon atoms, preferably an alkyl group having 1 to 7 carbon atoms.
R" is hydrogen or R,
B is —R or —OH or —OR or —TNHCH$_2$CH$_2$NHR",
C is —OH or —OR,
D is —R, —OH or —OR,
T is a divalent hydrocarbon group having 1 to 8 carbon atoms, preferably an alkylene group having 1 to 4 carbon atoms,
p, q and r are positive integers, the sum of p, q and r being from 10 to 300, and
in which preferably at least two primary amino groups are present.

The second of the two types of polysiloxanes is an amino-functional polysiloxane (Type II) having the following composition:

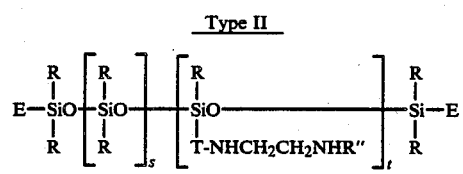

Type II in which
R is a monovalent hydrocarbon group having 1 to 20 carbon atoms, preferably an alkyl group having 1 to 7 carbon atoms,
R" is hydrogen or R,
T is a divalent hydrocarbon group having 1 to 8 carbon atoms, preferably an alkylene group having 1 to 4 carbon atoms,
E is —R or T—NHCH$_2$CH$_2$NHR",
s and t are positive integers, the sum of s and t being from 10 to 300, and t is at least 2, and
in which preferably at least two primary amine groups are present.

The molar ratio of Type I to Type II polysiloxane in the composition is from 4:1 to 1:9.

Polymers of Type I are commercially available, such as 478, 531, and Softener CSF, all from Dow Corning; and 1705 from General Electric as well as SWS-756.

Polymers of Type II are also commercially available, such as Q2-8220 from Dow Corning.

The third essential component of the composition is a cross-linking agent in the form of a water-soluble compound containing at least two carboxyl groups such as malonic, succinic, maleic, citric, glutaric, glutamic, phthalic, 4-hydroxyisophthalic acid or the like. The cross-linking agent is desirably non-toxic and non-irritating to the skin in the concentration employed. While there is no critical lower limit to the water solubility of the cross-linking agent, a solubility below about 0.01% by weight at 20° C. is generally impractical; preferably the cross-linking agent has a solubility in water of at least 0.1% by weight at 20° C.

The amount of cross-linking agent in the composition may vary over a wide range. In general, it is desirable that the molar quantity of the cross-linking agent be from 0.6% to 90% by weight of the total weight of polysiloxane present in the composition, preferably from 10 to 30% by weight.

The polysiloxanes employed in the present invention are essentially insoluble in water. Although applicants do not wish to be bound to any particular theory of the mode of operation or functioning of the composition, it is believed that the hydroxy or alkoxy groups of the Type I polymer condense with each other before application to the hair, and that a chemical reaction occurs between the amino groups of both types of polysiloxane and the carboxyl groups of the cross-linking agent resulting in partial covalent cross-linking of the two types of polysiloxane or evaporation of water and formation of a film or coating, thus producing a unique combination of advantageous properties in the film or coating.

The dispersions are prepared by first mixing together the Type I and Type II polysiloxanes in the desired proportions; if desired, a volatile organic solvent, preferably one having a boiling point below that of water, may be added to facilitate mixing. Among suitable solvents are alcohols such as methyl alcohol, ethyl alcohol and isopropyl alcohol. The amount of solvent used is not critical; however, it is desired that the solution be sufficiently dilute so as to facilitate mixing of the polysiloxanes and the eventual emulsification of the polysiloxane mixture in water. These organic solvents may remain in the composition or may be removed by heat or by evaporation under reduced pressure. It is undesirable to use a large excess of solvent because of the cost and difficulty of removing it during formation of the desired dispersion. Preferably no solvent is added and the two types of polysiloxane are simply mixed together.

To the mixture of polysiloxanes with or without an organic solvent may be added any desired filler, thickener, plasticizer, perfume, conditioner, wetting agent or soap, or other active agent for treating hair.

To convert the mixture to a dispersion, it is mixed with water or with an aqueous solution containing additional optional desired components or active agents, then subjected to severe mechanical mixing or shearing stress, for example in a Waring Blender or by sonication. It is also desirable to include in the mixture in order to facilitate formation of the dispersion a surfactant or surface active agent as a dispersing aid and stabilizer. Suitable surfactants include cationic, anionic or amphoteric surface active agents, the non-ionic surface active agents being preferred. Suitable agents include among others sodium lauryl sulfate, sodium dodecyl sulfate, polyoxyethylene (23) lauryl ether, polyoxyethylene stearate, and the like. The amount of surface active agent employed may vary depending upon the particular polysiloxanes and particular surface active agent used as well as on the particle size of the dispersion, and can readily be determined in any particular case by simple tests as is well known to those skilled in the art of preparing aqueous dispersions generally. The surface active agent may be dissolved in the polysiloxanes, or in the organic solvent solution or it may be dissolved or dispersed in water, after which the mixture or solution of polysiloxanes and water are thoroughly mixed by mechanical or sonication devices to form an aqueous dispersion and any organic solvent present is thereupon removed by evaporation. In order to hasten the removal of solvent, when present, the dispersion may be subjected to reduced pressure and/or heated to its boiling point. At this point the cross linking agent is either dissolved directly in the solution or is added to the dispersion as an aqueous solution along with other optional ingredients.

The relative proportion of total polysiloxane to water or other liquid in the dispersion may vary over a range from about 0.25% to about 30% by weight; for best results the concentration of total polysiloxanes in the dispersion should be from about 1.0% to about 15% by weight, most preferably from 1.0 to 5% by weight. The amount of dispersion applied to the hair may vary widely depending upon individual preferences, the manner of application, whether by spray or as a lotion or mousse, and the concentration of the polysiloxanes in the dispersion. If desired, the dispersion may be packaged with a conventional pressure propellent to enable it to be applied as a spray or aerosol foam.

When the composition of this invention is applied to hair and allowed to dry, without subsequent rinsing with water, the film formed by the composition supplies desirable characteristics to the hair including a high sheen, good tactile properties and ease of combing even when wet, in addition to set retention when the hair is exposed either to dry conditions or to an atmosphere of high humidity and to repeated combing. In general, the Type I polysiloxane acts to increase the firmness and elasticity of the film formed from the dispersion on the hair, and the Type II polysiloxane acts to make the film easily removable by washing with aqueous soap solution or shampooing.

The composition of the present invention is further distinquished from those of the prior art in its rapid drying or solidifying time, high durability in conditions of high humidity or when subjected to water rinse or combing, and remarkable ease of removal by conventional shampooing or washing with aqueous solutions of soap or other effective surface active agents.

The following specific examples are intended to illustrate more fully the nature of the invention without acting as a limitation upon its scope.

EXAMPLE 1

A hair styling and conditioning composition designed to be applied in the form of a foam from a container pressurized with a liquified pressure propellant was prepared as follows:

A hair styling aid was formed by mixing 1.95 g of Dow Corning 478 Fluid (an amino methoxy-functional dimethylsilicone) (Type I) and 1.05 g of Dow Corning Q2-8220 Fluid (an amino-functional dimethylsilicone)

(Type II). A solution of 0.3 g of a nonionic surfactant polyoxyethylene (23) lauryl ether (Brij 35 sp) and 46.7 g distilled water was slowly added to the mixture of silicones and the mixture was subjected to severe shear mixing until a stable milk white emulsion was produced. A solution of 0.7 g of succinic acid, 0.1 g cocamide DEA (a foaming agent) and 49.2 g distilled water was mixed with the silicone emulsion. This mixture was placed in an aerosol can and propellant (15% propane, 82% isobutane, 3% n-butane) was added at a propellant-to-liquid ratio of 7 to 93. When released from the container through a conventional valve, this resulted in a fine textured foam which could be easily applied to wet or dry hair.

To demonstrate the efficacy of the composition in maintaining hair in a desired configuration, the following test was performed. Nine tresses, each 1 g in weight and 5" in length, were shampooed with White Rain Shampoo. There was applied to each of three of these tresses 0.4 g of a commercially available mousse (Mink Difference Mousse (regular)). The tresses were rolled on ¼" diameter rollers. This process was repeated using the foam of the preceding paragraph in place of the mousse on three more tresses. The last three tresses were rolled on ¼" diameter curlers immediately after shampooing. All nine tresses were stored 18 hours at ambient temperature, on the rollers. Subsequently, the rollers were removed from the three tresses which had received only shampoo treatment. These curls were sprayed with a commercially available (Gillette) aerosol hair spray set-holding resin composition (ethyl ester of PVM/MA copolymer) for 5 seconds from a distance of 10". The roller was then replaced in the curl.

All nine curls were equilibrated for 30 minutes in a 70°, 65% relative humidity chamber, then the rollers were removed from the curls. The curls treated with mousse and hair spray set-holding resin were very stiff and difficult to comb. The curls treated with the foam were silky, soft, and easy to comb. The curls were combed through once and their length measured. This was taken as the initial length (Lo). The curls were placed in the 70°, 65% RH chamber, combed through once every hour and then were remeasured after 6 hours (Lt). The % curl retention was then calculated using the formula below:

$$\text{Curl Retention} = \frac{L - Lt}{L - Lo} \quad \begin{array}{l} L = \text{fully extended length of hair \%} \\ Lo = \text{initial curl length} \\ Lt = \text{curl length at Time } t \end{array}$$

Results are given in Table I:

TABLE I

| | % Curl Retention (Ave. of 3 Tresses) |
|---|---|
| Foam Composition | 77% |
| Hairspray set-holding resin | 73% |
| Mousse | 68% |

EXAMPLE 2

Two hair treatment compositions, encompassed by this invention, were produced as described below. For Hair Treatment Composition A (HTC-A), 1.804 g of Dow Corning 478 Fluid (an amino alkoxyfunctional dimethylsilicone) and 0.971 g of Dow Corning Q2-8220 Fluid (an amino functional dimethylsilicone) were mixed together. A solution of 0.278 g of PEG-50 stearate (a nonionic surfactant) and 46.947 g of distilled water was added slowly to the mixture of silicones. This mixture was subjected to high shear mixing until a stable, milk white emulsion was produced. A solution of 0.061 g of succinic acid, 0.069 g of Cocamide DEA (a foaming agent) and 42.370 g distilled water was mixed with the silicone emulsion producing a stable, translucent emulsion. This emulsion was placed in an aerosol can with 7.5 g of propellant A-46 (a mixture of isobutane, butane, and propane). This mixture produced a foam (HTC-A) when released from the can through a conventional valve.

For Hair Treatment Composition B (HTC-B), 2.405 g of Dow Corning 478 Fluid and 1.295 g of Dow Corning Q2-8220 Fluid were mixed. A solution of 0.370 g PEG-50 stearate and 42.138 g distilled water was slowly added to the mixture of silicones. This mixture was also subjected to higher-shear mixing until a stable, white emulsion was produced. A solution of 0.925 g gelatin (cosmetic grade, a thickening agent), 0.139 g of cocamide DEA>0.492 g succinic acid and 44.736 g distilled water were mixed with the silicone emulsion. The emulsion was placed in an aerosol can together with 7.500 g of propellant A46. The mixture produced a foam (HTC-B) when released from the can.

On an extremely hot, humid day (temperature 90°-99° F., humidity 90%), a professional hair stylist styled the hair of four black women. The models' hair was shampooed, towel dried and HTC-A and -B were worked through the damp hair, HTC-A on the left side, and HTC-B on the right side of each. The hair was then blown dry and curled with curling irons. The stylist judged the wet and dry combing of hair treated with HTC-A or -B to be highly unusual and easier in comparison to hair treated with commercially available styling mousses and lotions. The models returned 24 hours later. The stylist and the models' evaluated the effectiveness of HTC-A and -B in maintaining curls in the extreme heat and humidity. The stylist and the models concluded that both compositions had completely maintained the curls in the high humidity and heat. Ethnic hair sprays and styling lotions, according to the models and stylist, would have maintained curls for less than two hours under such conditions.

What is claimed is:

1. A composition comprising a liquid aqueous vehicle having dispersed therein from 0.25 to 30% by weight of a mixture comprising two types of polysiloxanes having the following average compositions:

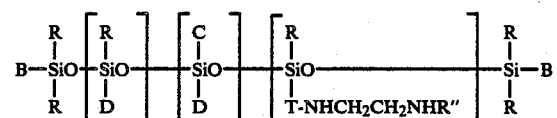

Type I in which

R is a monovalent hydrocarbon group having 1 to 20 carbon atoms.

R" is hydrogen or R

B is —R or —OH or —OR or —TNHCH$_2$CH$_2$NHR"

C is —OH or —OR

D is —R, —OH, or —OR

T is a divalent hydrocarbon group having 1 to 8 carbon atoms p, q and r are positive integers, the sum of p, q or r being from 10 to 300, Type II

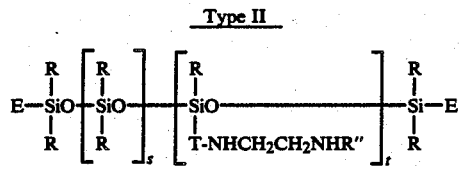

in which
R is a monovalent hydrocarbon group having 1 to 20 carbon atoms,
R" is hydrogen or R,
T is a divalent hydrocarbon group having 1 to 8 carbon atoms, preferably an alkylene group having 1 to 4 carbon atoms, E is —OR or —T—NHCH$_2$CH$_2$NHR",
s and t are positive integers, the sum of s and t being from 10 to 300, and t is at least 2, and the molar ratio of Type I to Type II being from 4:1 to and a cross-linking agent comprising a water-soluble compound containing at least two carboxyl groups, the amount of said agent being from 0.6 to 90% by weight of total polysiloxane.

2. A composition as claimed in claim 1 in which a dispersing agent is included in the composition.

3. A composition as claimed in claim 2 in which R is an alkyl or benzyl group having 1 to 7 carbon atoms, R' is an alkyl group having 1 to 4 carbon atoms, T is an alkylene group having 1 to 4 carbon atoms, and in which T is an alkylene group having 1 to 4 carbon atoms.

4. A composition as claimed in claims 1, 2 or 3 in which said cross-linking agent is succinic acid.

5. A composition as claimed in claim 1 in which R is an alkyl group having 1 to 7 carbon atoms.

* * * * *

UNITED STATES PATENT AND TRADEMARK OFFICE
CERTIFICATE OF CORRECTION

PATENT NO. : 4,915,938

DATED : April 10, 1990

INVENTOR(S) : Mary E. Zawadzki

It is certified that error appears in the above-identified patent and that said Letters Patent is hereby corrected as shown below:

Col. 2, line 27, Insert --R-- before "is a "monovalent hydrocarbon"

Col. 7, line 3, Delete "or" and insert --and--

Col. 8, line 4, Insert --1:9-- after "from 4:1 to"

Signed and Sealed this

Seventeenth Day of March, 1992

Attest:

HARRY F. MANBECK. JR.

Attesting Officer     Commissioner of Patents and Trademarks